US012233277B2

(12) United States Patent
Ring et al.

(10) Patent No.: US 12,233,277 B2
(45) Date of Patent: Feb. 25, 2025

(54) BRAIN STIMULATION APPARATUS, METHOD, AND MEDIUM

(71) Applicant: Wave Neuroscience, Inc., Newport Beach, CA (US)

(72) Inventors: Alexander Ring, Newport Beach, CA (US); James William Phillips, Fountain Valley, CA (US)

(73) Assignee: Wave Neuroscience, Inc., Newport Beach, CA (US)

( * ) Notice: Subject to any disclaimer, the term of this patent is extended or adjusted under 35 U.S.C. 154(b) by 947 days.

(21) Appl. No.: 17/330,318

(22) Filed: May 25, 2021

(65) Prior Publication Data

US 2022/0379132 A1 Dec. 1, 2022

(51) Int. Cl.
*A61N 2/00* (2006.01)
*A61N 2/12* (2006.01)
*G06N 3/02* (2006.01)
*G16H 20/40* (2018.01)
*G16H 40/63* (2018.01)
*G16H 50/30* (2018.01)

(52) U.S. Cl.
CPC ............ *A61N 2/006* (2013.01); *G06N 3/02* (2013.01); *G16H 20/40* (2018.01); *G16H 40/63* (2018.01); *G16H 50/30* (2018.01); *A61N 2/12* (2013.01)

(58) Field of Classification Search
None
See application file for complete search history.

(56) References Cited

U.S. PATENT DOCUMENTS

| 6,463,328 | B1 | 10/2002 | John |
| 8,475,354 | B2 | 7/2013 | Phillips et al. |
| 8,585,568 | B2 | 11/2013 | Phillips et al. |
| 8,926,490 | B2 | 1/2015 | Phillips et al. |
| 9,015,057 | B2 | 4/2015 | Phillips et al. |
| 9,308,385 | B2 | 4/2016 | Jin |

(Continued)

FOREIGN PATENT DOCUMENTS

WO 2022251851 A1 12/2022

OTHER PUBLICATIONS

International Preliminary Report on Patentability for International Application No. PCT/US2022/072571, dated Dec. 7, 2023, 6 Pages.

*Primary Examiner* — Thaddeus B Cox
(74) *Attorney, Agent, or Firm* — K&L Gates LLP; Brian J. Novak; Dennis A. Majewski (57) ABSTRACT

An apparatus and method configured to control a brain stimulation device. The apparatus and method include a brain stimulation apparatus including, an input unit configured to receive at least one biological metric measurement value of a user, a neural network unit configured to determine a treatment pulse frequency equal to a weighted sum of the at least one biological metric measurement value of the user, wherein the weighted sum includes a plurality of weighting factors corresponding to each of the at least one biological metric measurement values, and wherein the plurality of weighting factors are determined based on optimized outcome results from previous administered treatments using treatment pulse frequencies determined by previous weighting factors, and a control unit configured to control a motor to operate at the treatment pulse frequency determined.

33 Claims, 4 Drawing Sheets

(56) References Cited

U.S. PATENT DOCUMENTS

| | | |
|---|---|---|
| 9,649,502 B2 | 5/2017 | Phillips et al. |
| 9,962,555 B1 | 5/2018 | Charles et al. |
| 10,342,986 B2 | 7/2019 | Jin |
| 10,350,783 B2 | 7/2019 | Kiljunen et al. |
| 2018/0110960 A1 | 4/2018 | Youngblood et al. |
| 2018/0221678 A1* | 8/2018 | Ilan ..................... A61N 2/006 |
| 2020/0038674 A1 | 2/2020 | John |
| 2021/0162217 A1* | 6/2021 | Rezai ................... A61N 1/0534 |
| 2021/0272664 A1* | 9/2021 | Carter ................... G16H 80/00 |
| 2022/0218942 A1* | 7/2022 | Jain ..................... A61M 21/02 |

* cited by examiner

BRAIN STIMULATION APPARATUS, METHOD, AND MEDIUM

BACKGROUND

Over the years, magnetic field treatment has grown in popularity as a method of treating physiological and mental disorders. As popularity for this type of treatment grows, it has shown that stimulating the brain with magnetic fields at specific frequencies produced therapeutic and advantageous effects. Some of these advantages include, but are not limited to, improved mood, better sleep, as well as increased performance in athletics and academics.

Currently, brain stimulation is generally delivered as a series of pulses, with a pre-determined amplitude, frequency, duty-cycle, and waveform where the pulse frequency is one of the more important parameters. An example of this is Repetitive Transcranial Magnetic Stimulation (rTMS) which uses an electromagnet that generates a series of alternating magnetic field pulses. U.S. Pat. No. 8,475,354 describes a method whereby rTMS provides a low amplitude magnetic field stimulation device that targets an intrinsic frequency of a specified EEG band. Although targeting an intrinsic frequency may be an effective treatment for mental disorders, the intrinsic EEG frequency is only one of several biological metrics that may be used to determine the optimal treatment frequency. Moreover, there is no evidence that stimulation with pulse frequency equal to the intrinsic frequency achieves optimal results.

SUMMARY OF THE INVENTION

The present disclosure relates to brain stimulation technology. Specifically, to brain stimulation including an artificial neural network for setting an optimal pulse frequency. Exemplary embodiments described herein may be used for determining an optimal treatment frequency based on biological metrics and outcome measures.

The various embodiments of the present brain stimulation apparatus and method, have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description of the Embodiments," one will understand how the brain stimulation apparatus and method of the present disclosure provide the advantages described herein.

In a first embodiment, a brain stimulation apparatus includes, an input unit configured to receive at least one biological metric measurement value of a user, a neural network unit configured to determine a treatment pulse frequency equal to a weighted sum of the at least one biological metric measurement value of the user, wherein the weighted sum includes a plurality of weighting factors corresponding to each of the at least one biological metric measurement values, and wherein the plurality of weighting factors are determined based on optimized outcome results from previous administered treatments using treatment pulse frequencies determined by previous weighting factors, and a motor control unit configured to control a motor to operate at the determined treatment pulse frequency.

In another embodiment, a brain stimulation method includes, receiving at least one biological metric measurement value of a user, determining a treatment pulse frequency equal to a weighted sum of the at least one biological metric measurement value of the user, wherein the weighted sum includes a plurality of weighting factors corresponding to each of the at least one biological metric measurement values, and wherein the plurality of weighting factors are determined based on optimized outcome results from previous administered treatments using treatment pulse frequencies determined by previous weighting factors, and controlling a motor to operate at the determined treatment pulse frequency.

DETAILED DESCRIPTION OF THE EMBODIMENTS

Example devices, methods and systems are described herein. Any example embodiment or feature described herein is not necessarily to be construed as preferred or advantageous over other embodiments or features. The example embodiments described herein are not meant to be limiting. It will be readily understood that certain aspects of the disclosed devices, systems and methods can be arranged and combined in a wide variety of different configurations, all of which are contemplated herein. For the avoidance of doubt, any embodiment, configuration, part, subpart, routine, method step described herein may be removed, added, or recombined with any other part, subpart, routine, method step, of any other embodiment or configuration as described herein. The exemplary embodiments are examples only and simply represent sample combinations of features.

Therefore, the particular arrangements shown in the figures should not be viewed as limiting. It should be understood that other embodiments might include more or less of each element shown in a given figure. Further, some of the illustrated elements may be combined or omitted. Yet further, an example embodiment may include elements that are not illustrated in the figures.

The present disclosure provides a brain stimulation device and method utilizing an artificial neural network to set an optimized treatment pulse frequency to treat a user. Thus, the brain stimulation device may be used to treat a vast array of physiological conditions and/or neuropsychiatric conditions.

In some embodiments, the physiological conditions treated can be, but are not limited to, concentration, sleep, alertness, memory, blood pressure, stress, libido, speech, motor function, physical performance, cognitive function, intelligence, height and/or weight.

In other embodiments, the neuropsychiatric conditions treated can be, but are not limited to, Autism Spectrum Disorder (ASD), Alzheimer's disease, ADHD, schizophrenia, anxiety, depression, coma, Parkinson's disease, substance abuse, bipolar disorder, a sleep disorder, an eating disorder, tinnitus, traumatic brain injury, post-traumatic stress syndrome and/or fibromyalgia.

Exemplary embodiments of the present disclosure provide for using an artificial neural network to determine and optimize a treatment pulse frequency to optimize brain stimulation during treatment. In an exemplary embodiment, an artificial neural network optimizes a set of weighting factors to determine a magnetic pulse frequency to achieve optimal brain stimulation.

Figure 1:
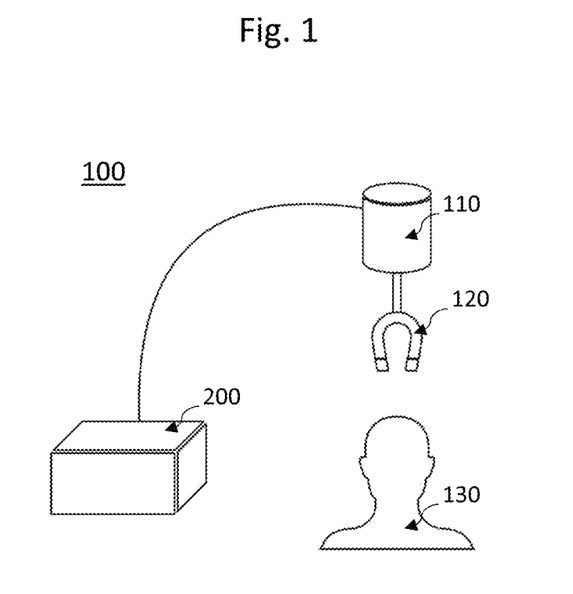
FIG. 1 shows a system for controlling a brain stimulation device according to an embodiment of the present disclosure.

FIG. 1 shows an exemplary system for controlling a brain stimulation device 100 according to an exemplary embodiment of the present disclosure.

In the exemplary embodiment, the brain stimulation device 100 is a Transcranial Magnetic Stimulation system. However, in other embodiments, the brain stimulation device 100 can be, but is not limited to, a transcranial Alternating Current Stimulation (tACS) system, an ultrasonic stimulation system, a vibration stimulation system, an optical stimulation system and/or an audio stimulation system.

Described herein, in certain embodiments, are devices and methods for modulating the electrical activity of a brain in a targeted manner using a weak magnetic field, generally field with a strength of less than about 100 Gauss. The magnetic field is varied over time in a periodic manner, generally with a frequency tuned to specifically affect one of the intrinsic frequencies of the brain, optionally the alpha frequency.

In one aspect described herein is a device for use in treating a subject, comprising: a Low Field Magnetic Stimulation (LFMS) device; wherein the LFMS device is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and wherein the device comprises a controller capable of adjusting the frequency or pulsing of the device.

In one aspect described herein is a device for use in treating a subject, comprising: a Magnetic Resonance Imaging (MRI) device; wherein the MRI device is capable of influencing (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, or (e) a combination thereof, and wherein the device comprises a controller capable of adjusting the frequency or pulsing of the device.

In one aspect described herein a device that may include a user interface; a waveform generator in communication with the user interface, wherein the waveform generator is capable of creating an electrical waveform; and at least one coil capable of converting the electrical waveform into a magnetic field. Alternatively, or in addition thereto, the system may include a permanent magnet with a controller for setting a deceleration, acceleration, rotation speed, rotation direction, or other attribute of the permanent magnet in order to generate a magnetic field having a waveform. The user interface can be used to adjust the waveform so that the resulting magnetic field is configured to influence (a) an intrinsic frequency of a brain of the subject within a specified Electroencephalography (EEG) band; (b) a Q-factor of an intrinsic frequency of a brain of the subject within a specified EEG band; (c) a coherence of intrinsic frequencies among multiple sites in a brain of the subject within a specified EEG band; (d) an EEG phase, (e) another attribute as determined by the neural network of the system to optimize the control parameter of the device, or (f) a combination thereof. In some embodiments, the device further comprises an amplifier capable of modifying the waveform.

In some embodiments, the brain is influenced with a Low Field Magnetic Stimulator (LFMS), a Magnetic Resonance Imager (MRI), a Transcranial Magnetic Stimulator (TMS), a Neuro-EEG Synchronization Therapy device, a picoTesla™ device, or any combination thereof.

In this example, the system includes, but is not limited to, a magnet 120 coupled to and rotated by a motor 110. A controller 200 may be communicatively coupled to the motor 110. In this example, the magnet 120 rotates so that the axis of rotation is generally perpendicular to the surface of the scalp of a user 130. Moreover, the motor 110 is coupled to the magnet 120 and rotates the magnet 120 in response to controls sent by the controller 200 to apply a magnetic field upon the user 130.

Although shown and described herein in terms of a permanent magnet, embodiments described herein are not so limited. Exemplary embodiments of a magnetic generation unit may include systems and devices that generate a varying magnetic such as a magnetic field having a waveform. Exemplary embodiments of a magnetic generation unit may include, but are not limited to, a movable permanent magnet, a variable current through a coil, and other electro-magnetic devices.

The applied magnetic field can be varied and controlled by changing parameters of the magnet's 120 rotation such as, but not limited to, the speed of rotation, the acceleration and/or deceleration of rotation, the time of rotation and the direction of rotation. For embodiments of a coil, the applied magnetic field can be varied and controlled by changing parameters of electric waveform supplied to the coil.

Figure 2:
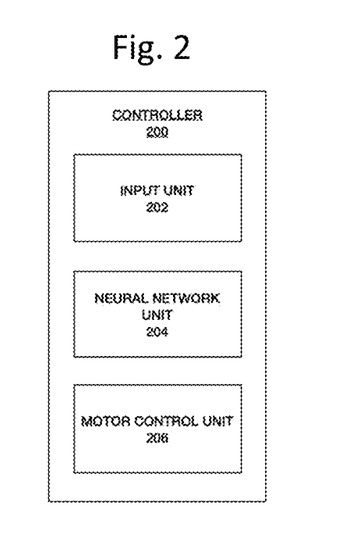
FIG. 2 shows a schematic diagram of a controller according to an embodiment of the present disclosure.

FIG. 2 shows a schematic diagram of a controller 200 according to an embodiment of the present disclosure. The controller 200 includes, but is not limited to, an input unit 202 to receive data, a neural network unit 204 and a motor control unit 206.

In an exemplary embodiment, the system may include a user interface. The user interface may be in combination with the input unit 202 and/or separated therefrom. The user interface can provide information regarding the operation of the device such as the strength of the magnetic field, the frequency of the change in the magnetic field, and the like. The user interface can be graphical, can be computer-based, can consist of controls such as buttons, dials, and the like, or any combination thereof. The user interface can be analog or digital. In some embodiments, the user interface provides a means to adjust and/or control parameters such as the strength of the magnetic field, the frequency of the change in the magnetic field, and the like. The user interface may include a controller, and/or a controller can comprise a user interface.

The input unit 202 is configured to receive an input from an operator of the system and/or directly from the user 130. The input can be, but is not limited, real time data and/or past acquired data to be used by the neural network unit 204. The input unit may include any combination of a communications port, data input, user input, sensors, processors, or memory for storing computer instructions and/or received data. The processor may execute instructions stored on memory to perform the functions described herein. For example, the input unit may receive data received through a communication port and store the received data in memory. The input unit may receive data from one or more sensors and generate input data from the sensor data to be used by the neural network according to embodiments described herein.

Various embodiments of the input unit 202 is contemplated herein. For instance, an exemplary embodiment may include a data port or other communication interface for receiving data to be used by the neural network unit. The data may be raw or processed information received from one or more channels of an EEG. An exemplary embodiment may include one or more electrodes for receiving EEG signals from a patient. An exemplary embodiment may include one or more sensors for receiving, detecting, determining, or otherwise obtaining a biological metric of a patent.

Additionally and/or alternatively, where EEG electrodes are present in the device and are capable of measuring the subject's brain waves, the treatment may be chosen automatically by the device based on the readings of the subject's brain waves prior to the treatment and based on a set of rules stored in the controller subunit. Additionally and/or alternatively, where EEG electrodes are present in the device and are capable of measuring the subject's brain waves, the controller subunit is capable of storing the output of the EEG electrodes prior to, during, and/or after treatment with the device. Additionally and/or alternatively, where EEG electrodes are present in the device and are capable of measuring the subject's brain waves, the controller subunit is capable of transmitting the output of the EEG electrodes prior to, during, and/or after treatment with the device. This transmitting may be real-time (during measurement), or after storage of the EEG electrode outputs and during an upload or download from the device.

In an embodiment of the present disclosure, inputted data generally relates to biological metrics applicable to the user 130. These biological metrics can include, but are not limited to, an intrinsic frequency of a predefined EEG band, EEG alpha power of a predefined EEG band, Q-factor of a pre-defined intrinsic frequency of a predefined EEG band, coherence of an EEG across a plurality of locations on the brain, phase of an EEG across a plurality of locations on the brain, ratio of a power of a first predefined EEG band and a power of a second predefined EEG band, heart rate, heart rate variability, breathing rate and breathing rate variability.

The neural network unit 204 may be communicatively-coupled to the input unit 202 and configured to receive the inputted data from the input unit 202 and determine an optimal treatment pulse frequency for the brain stimulation device 100 for treatment of the user 130. Additionally, the neural network unit 204 is communicatively-coupled to the motor control unit 206 and is configured to send/receive control data to the motor control unit 206 based on the optimal treatment pulse frequency.

In an embodiment of the present disclosure, an optimal pulse frequency is determined by the neural network unit 204 and an appropriate control signal is sent to the motor control unit 206 to achieve the optimal treatment pulse frequency.

In an exemplary embodiment, the motor control unit 206 is communicatively-coupled to the neural network unit 204 and configured to send/receive control data including the optimal treatment pulse frequency. Moreover, the motor control unit 206 is coupled to the motor 110 to operate the motor 110 based on the control data received from the neural network unit 204.

For example, in an exemplary embodiment, a magnet may be mounted by a frame to a base. This allows the magnet to be held stationary as the device treats a subject whose head may be positioned near to the magnet (within the magnetic field produced by the magnet). The magnet may be coupled to the controller subunit by a drive shaft. The drive shaft may couple to a motor in communication with the controller subunit by a coupling. The coupling may allow for various magnet arrangements to be interchanged by merely decoupling the drive shaft from the controller subunit and coupling a device having another arrangement of magnets. The magnet may be controlled by the controller subunit through the motor that may be driven by a motor driver. The motor driver may be coupled (directly or indirectly) to a power supply. The motor driver, which can control, for non-limiting example, the speed, direction, acceleration, deceleration, etc., of the magnet through the drive shaft, can be directed and/or monitored by controls such as, for example, a device speed control, an on/off control, a display, a random/continuous control, and a high/low control. A user and/or the system (such as using the neural network) can adjust each of these controls, which are coupled to a processor circuit board and thus coupled to the motor driver.

As described herein, the drive shaft and/or the magnet(s) may be controlled automatically based on a prescribed treatment (time of treatment, frequency of magnet rotation, etc.) that is downloaded and/or programmed into the processor circuit board and/or generated by the neural network unit. For example, operation of the motor 110 is based on data received by the motor control unit 206 from the neural network unit 204. The motor 110 then moves the magnet 120 according to the optimal treatment pulse frequency determined by the neural network unit 204.

Figure 3:
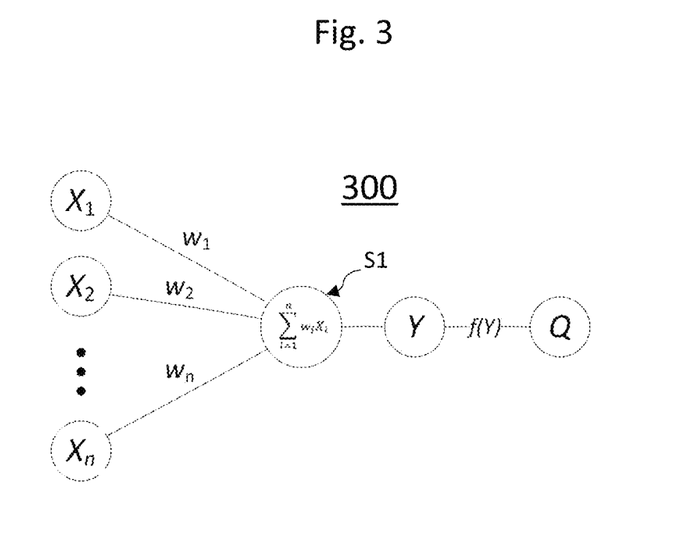
FIG. 3 depicts operation of a neural network unit according to an embodiment of the present disclosure.

FIG. 3 depicts operation of the neural network unit 204 according to an embodiment of the present disclosure. The neural network unit 204 is configured to incorporate an artificial neural network (ANN) 300 according to the exemplary embodiment of the present disclosure.

Here, the ANN 300 includes, but is not limited to, a plurality of weighting factors W1 and W2-Wn, a weighted sum S1 of the plurality of weighting factors W1 and W2-Wn, a treatment pulse frequency Y, and a weighted sum of outcomes Q.

In an exemplary embodiment, the plurality of weighting factors W1 and W2-Wn are for biological metrics X1 and X2-Xn of the user 130 receiving magnetic pulse therapy. The biological metrics X1 and X2-Xn can include, but are not limited to, EEG alpha frequency, EEG alpha power, and Heart Rate Variability (HRV). Other biological metrics may include, any combination of an intrinsic frequency of a predefined EEG band, EEG alpha power of a predefined EEG band, Q-factor of a pre-defined intrinsic frequency of a predefined EEG band, coherence of an EEG across a plurality of locations on the brain, phase of an EEG across a plurality of locations on the brain, ratio of a power of a first predefined EEG band and a power of a second predefined EEG band, heart rate, heart rate variability, breathing rate and breathing rate variability.

Moreover, the treatment pulse frequency Y of the ANN 300 is a weighted sum S1 of the plurality of weighting factors W1 and W2-Wn. In the exemplary embodiment of the present disclosure, the weighting factors W are the biological metrics of the user 130 and the user's 130 body and brain are affected by the treatment which alters one or more outcomes. Thus, the treatment pulse frequency Y is set to a weighted sum S1 of the biological metrics.

In one embodiment, the weighted sum S1 of the plurality of weighting factors is calculated using the equation:

$$\sum_{i=1}^{n} w_i X_i$$

In the ANN 300, Q is a weighted sum of the outcomes where the weighting coefficients are selected based on the significance of the outcome.

For example, where it is expected that treatment will result in a decrease in a user's 130 depression rating scale, an increase in the cognitive battery, and an increase in HRV, and the decrease in the user's 130 depression rating scale is the most important outcome. The weighting coefficient for this outcome in the calculation of Q will be high compared to the weighting factor for the other outcomes.

In some embodiments, outcomes include, but are not limited to, changes in value of one or a combination of measures such as a psychological rating scale and/or a biological metric.

Examples of psychological ratings can include, but are not limited to, a depression Rating Scale score, an anxiety Rating Scale score, an autism Rating Scale score, a Post-Traumatic Stress Disorder (PTSD) Rating Scale score, a Quality of Life Rating Scale score, a scholastic examination score and/a cognitive battery test score.

In the exemplary embodiment, the plurality of weighting factors W1 and W2-Wn for the calculation of the treatment pulse frequency Y are optimized based on previous treatments. Thus, to optimize these weighting factors W1 and W2-Wn, treatments to be evaluated should use the same biological metrics, same outcomes and Q calculation. Otherwise, the optimization may be made using data that does not reflect a user's 130 true characteristics.

Figure 4:
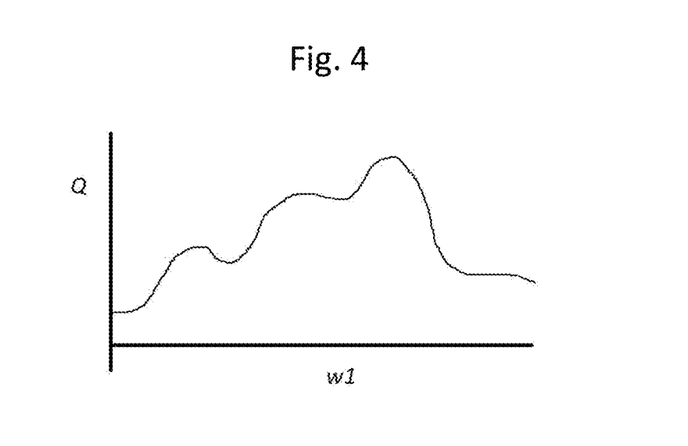
FIG. 4 shows a graph of an optimization according to an embodiment of the present disclosure.

FIG. 4 shows a graph of an optimization according to a first embodiment of the present disclosure. Here, ANN 300 uses one biological weighting factor W1.

In this example, if the weighing factor w1 is alpha frequency of the user 130 and Q is the decrease in Hamilton Depression Rating Scale score, then in the ANN 300, the weighting factor w1 can be chosen to maximize the change before and after treatment. This can be either based on the outcomes of a single user 130 to treatment, or it can be performed over a population including a plurality of users.

In either case, decrease is not necessarily deterministic, and the same w1 value may achieve a different Q value for different users, or for the same user 130 at different times. Therefore, outcomes of the ANN 300 can be considered stochastic and optimization can take into account variability. To achieve this, adjustments to w1 may be made based on moving averages of outcomes and not only based on a single measurement.

Figure 5:
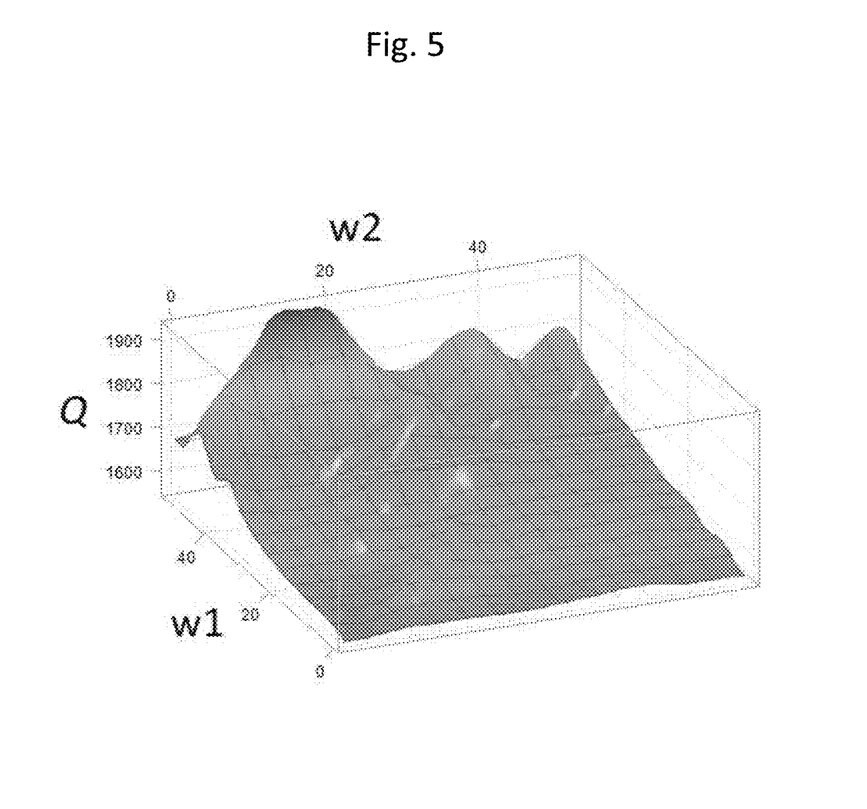
FIG. 5 shows a graph of an optimization according to an embodiment of the present disclosure.

FIG. 5 shows a graph of an optimization according to a second embodiment of the present disclosure. This embodiment shares similar elements as those described above, as such, their descriptions will be omitted and only differences will be described herein.

In this example, optimization is performed by the ANN 300 similarly to FIG. 3 but instead, a plurality of weighting factors are used. Weighing factors w1 and w2 are both biological metrics of user 130 and optimization by the ANN 300 is performed to find w1 and w2 that result in the maximum Q.

In one embodiment, the preferred method of optimizing weighting factors W is through iterative techniques. For example, the ANN 300 uses finite differences where the difference in Q between a difference quotient is calculated as:

$$[f(W+a)-f(W-a)]/|b-a|$$

Assuming a single weighting factor, then w, a, and b are all scalars. In this example, the difference quotient gives an indication as to the slope or derivative of the curve for Q near w.

In some embodiments, finite differences are used, such as, but not limited to, Newton's method, Sequential quadratic programming and/or Interior point methods.

In other embodiments, optimization of weighting factors W is through iterative techniques including, but not limited to: coordinate descent methods, conjugate gradient methods, gradient descent, sub gradient methods, bundle method of descent, ellipsoid method, conditional gradient method, quasi-Newton methods, simultaneous perturbation stochastic approximation, interpolation methods and/or pattern search methods. Additionally, stochastic methods are used including, but not limited to, simulated annealing, mean field annealing, stochastic approximation and stochastic gradient descent.

In determining the global maximum in the present embodiment, it is desirable that initial estimates for weighting factors W be chosen to improve chances of being close to optimum. For example, it may be likely that one biological metric is more important in achieving superior outcomes compared to other biological metrics used. In this case, a good starting approximation for weighting factors W is to set less relevant weighting factors to zero, and to initially optimize over the weighting factor used with the most relevant biological metric.

In an exemplary embodiment of the present disclosure, biological metrics are prioritized based on expected importance in determining an optimal treatment frequency that results in the best outcome. Optimization is first determined over the first priority biological metric with all other weighting factors set to 0. Then, optimization is determined over the next priority biological metric, with the weighting factor for the first priority biological metric set equal to the value that achieved the optimal outcome, and all others set to zero. Finally, optimization is determined over the next priority biological metric, with all others kept at their existing values. Eventually, optimization will occur over all weighting factors for all biological metrics.

Figure 6:
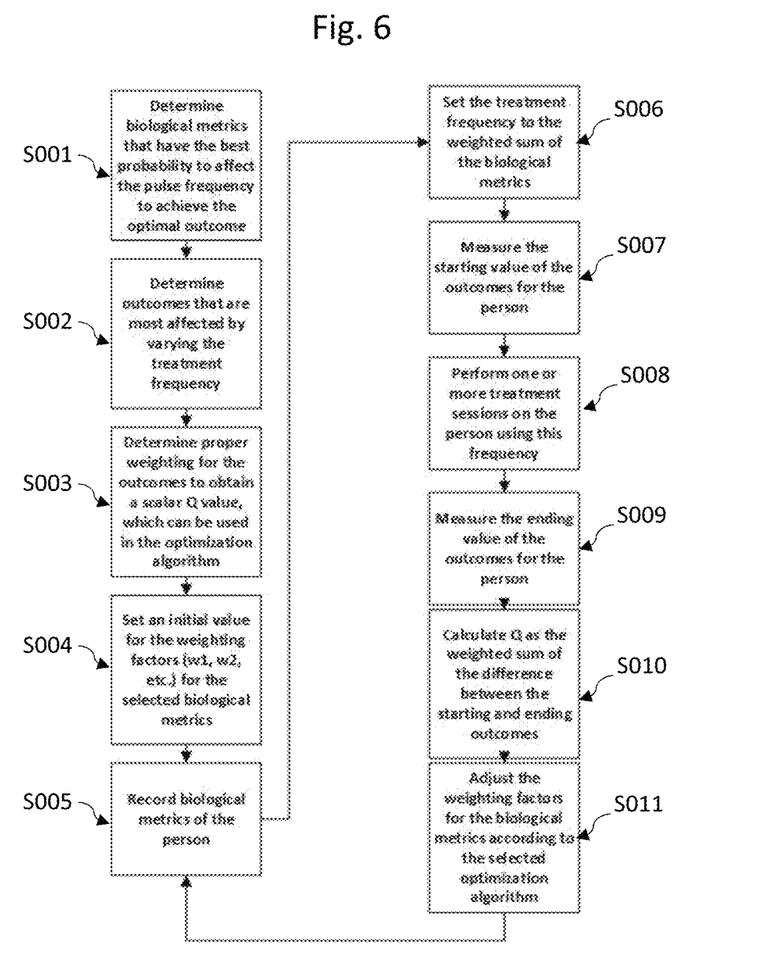
FIG. 6 shows a flowchart for optimization by an artificial neural network according to an embodiment of the present disclosure.

FIG. 6 shows a flowchart for optimization by the ANN 300 according to an embodiment of the present disclosure.

In the exemplary embodiment, in Step S001, the proper biological metrics, outcomes, and outcome weighting factors are first determined based on present knowledge of what has the greatest effect on the efficacy of treatment type. This includes, but is not limited to, the probability to affect treatment pulse frequency.

Next, in Step S002, a determination of outcomes most affected is made based on current knowledge of treatment type. For example, this can include knowledge from past treatments by the current user 130 or past treatments by others in similar circumstances.

Then in Step S003, weighting factors may be selected with polarity (positive or negative) designation such that when the weighting factors are multiplied by the difference of a starting outcome and ending outcome, the result is positive if the difference is an improvement. These may be adjusted as more people are treated. Additionally, more biological metrics, outcomes, and outcome weighting factors may be included or omitted.

In Step S004, an initial value for the weighting factors for each of the plurality of biological metrics is chosen based on which biological metrics are believed to have the most effect on the efficacy of stimulation.

As described herein, exemplary embodiments may be used to set initial values for the weighting factors. For example, a set of weighting factors may be selected based on prior experience or settings. In an exemplary embodiment, the set of weighting factors may be set according to the last treatment session of the user. As another example, the system may determine optimized initial starting values for the weighting factors. The weighting factors may be considered sequentially based on a priority of the biological metric to affect the pulse frequency and achieve the optimal outcome. The weighting factor for the highest priority biological metric may be set to a non-zero value, and the remaining weighting factors set to zero to optimize the weighting factor of the highest priority biological metric. The next highest priority biological metric may then have its weighting factor set to a non-zero weighting factor, and the highest priority biological metric may be set according to an optimized weighting value as determined in the prior step, while all other remaining weighting factors for the biological metric below in priority to the next highest priority biological metric are set to zero. The system may run sequentially through all of the weighting factors associated with each biological metric by setting all the weighting factors for biological metrics at a higher priority to the current biological metric according to the determined weighting factor of a preceding iteration, and all weighting factors lower in priority to the current biological metric to zero, to determine a weighting factor to apply to the current biological metric. The routine may then sequentially cycle to determine an initial weighting factor for each of the biological metric by determining the weighting factor for each of the biological metrics in order of the assigned priority of the biological metric.

Then in Step S005, initial biological metrics of the user 130 are measured and recorded. After recording, in Step S006 the treatment pulse frequency is set to the weighted sum of the biological metrics of the user 130 determined by the ANN 300.

In Step S007, the starting value of the outcome measurements are taken and recorded for the user 130. Then in Step S008 one or more treatment sessions are administered to the user 130 based on the calculated treatment pulse frequency. Afterwards, in Step S009 an ending value of the outcomes is measured and recorded for the user 130.

Next, in Step S010 a Q value is calculated as the weighted sum of the difference in values between starting outcome and ending outcome. In some embodiments, the difference between starting outcome and ending outcome may be an arithmetic difference or a percentage difference. In other embodiments, scaling methods may be used to adjust to characteristics of people undergoing treatment.

For example, someone may be treated with a Hamilton Depression rating score of 25, which is considered majorly depressed. Another person may have a Hamilton Depression rating score of 15, which is only minorly depressed. The scores may be normalized to an arbitrary initial value to make the changes more comparable in the algorithm, or percent difference may be used instead of arithmetic difference in order to make the differences more comparable.

Lastly, in Step S0011 the plurality of weighting factors are adjusted based on the particular optimization routine chosen. Upon adjusting the weighting factors, flow returns back to Step S0005 to record the biological metrics of the user 130 based on the newly set weighting factors.

In another embodiment, after adjusting the weighting factors in Step S0011, flow returns back to Step S005 with a new user 130 and biological metrics of the new user 130 are recorded based on the newly set weighting factors.

Pursuant to these exemplary embodiments, a brain stimulation device 100 and method is provided utilizing an artificial neural network to set an optimized treatment pulse frequency to treat a user 130.

The functions of the above-described exemplary embodiments can also be realized by supplying a program code for performing the processing of the above-described exemplary embodiments to a system or an apparatus and executing the program code by a computer (or a CPU or an MPU) of the system or the apparatus. In this case, the program code itself read out from a storage medium realizes the functions of the above-described exemplary embodiments, and also the storage medium that stores the program code also realizes the functions of the above-described exemplary embodiments.

In addition, the configuration includes a case where the program code for realizing the functions of the above-described exemplary embodiments may be executed by a single computer (or a CPU or an MPU) and a case where the program code may be executed by a plurality of computers in cooperation with each other. Furthermore, the configuration includes a case where the program code may be executed by a computer, or hardware such as a circuit configured to realize the functions of the program code may be provided. As an alternative to the above, the configuration includes a case where part of the program code may be realized by hardware, and the remaining part may be realized by computer software executed by the computer hardware.

Lastly, embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Exemplary embodiments of systems that may take advantage of embodiments described herein may include, without limitation those described by U.S. Pat. Nos. 8,475,354; 8,585,568; 8,926,490; 9,015,057; 9,308,385; 9,649,502; 9,962,555; 10,342,986; and 10,350,783, each of which are incorporated by reference in there entirety herein along with any other patent or publication disclosed herein.

While the present disclosure has been described with reference to exemplary embodiments, it is to be understood that the invention is not limited to the disclosed exemplary embodiments. The scope of the following claims is to be accorded the broadest interpretation to encompass all modifications, equivalent structures and functions.

What is claimed is:

1. A brain stimulation apparatus, comprising:
an input unit configured to receive at least one biological metric measurement value of a user;
a neural network unit configured to determine a treatment pulse frequency equal to a weighted sum of the at least one biological metric measurement value of the user,
wherein the weighted sum includes a plurality of weighting factors individually corresponding to one of the at least one biological metric measurement values, and
wherein the neural network unit is configured to determine the plurality of weighting factors based on optimized outcome results from previous administered treatments using treatment pulse frequencies determined by previous weighting factors; and
a magnetic generation unit configured to apply a varying magnetic field to the user; and
a control unit configured to control the varying magnetic field at the determined treatment pulse frequency.

2. The brain stimulation apparatus according to claim 1, wherein the previous weighting factors of the optimized outcome results from previous administered treatments are from the user.

3. The brain stimulation apparatus according to claim 1, wherein the previous weighting factors of the optimized outcome results from previous administered treatments are from another user.

4. The brain stimulation apparatus according to claim 1, wherein the at least one biological metric measurement value is a measurement of an intrinsic frequency of a predefined electroencephalogram band.

5. The brain stimulation apparatus according to claim 4, wherein the predefined electroencephalogram band is an alpha band, theta band, gamma band, beta band, or mu band.

6. The brain stimulation apparatus according to claim 1, wherein the at least one biological metric measurement value is a measurement of an electroencephalogram alpha power of a predefined electroencephalogram band.

7. The brain stimulation apparatus according to claim 1, wherein the at least one biological metric measurement value is a measurement of a Q-factor of a pre-defined intrinsic frequency of a predefined electroencephalogram band.

8. The brain stimulation apparatus according to claim 1, wherein the at least one biological metric measurement value is a measurement of coherence of an electroencephalogram across a plurality of locations on the brain of the user.

9. The brain stimulation apparatus according to claim 1, wherein the at least one biological metric measurement value is a measurement of phase of an electroencephalogram across a plurality of locations on the brain of the user.

10. The brain stimulation apparatus according to claim 1, wherein the at least one biological metric measurement value is a ratio of a power of a first predefined electroencephalogram band and a power of a second predefined electroencephalogram band.

11. The brain stimulation apparatus according to claim 1, wherein the at least one biological metric measurement value is a measurement of heart rate variability.

12. The brain stimulation apparatus according to claim 1, wherein the at least one biological metric measurement value is a measurement of breathing rate variability.

13. The brain stimulation apparatus according to claim 1, wherein the optimized outcome results are changes in value of measurements of at least one of,
a psychological rating scale,
a biological metric,
a cognitive battery test score, or
a Quality of Life rating scale score.

14. The brain stimulation apparatus according to claim 13, wherein the outcome results are changes in value of measurements recorded before and after one or more treatment sessions.

15. The brain stimulation apparatus according to claim 1, wherein the plurality of weighting factors are determined based on iterative optimization.

16. The brain stimulation apparatus according to claim 1, wherein the plurality of weighting factors are determined based on stochastic optimization.

17. A brain stimulation method, comprising:
receiving at least one biological metric measurement value of a user;
determining a treatment pulse frequency equal to a weighted sum of the at least one biological metric measurement value of the user,
wherein the weighted sum includes a plurality of weighting factors individually corresponding to one of the at least one biological metric measurement values, and
wherein the plurality of weighting factors is determined based on optimized outcome results from previous administered treatments using treatment pulse frequencies determined by previous weighting factors; and
controlling a motor to operate at the treatment pulse frequency determined.

18. The brain stimulation method according to claim 17, wherein the previous weighting factors of the optimized outcome results from previous administered treatments are from the user.

19. The brain stimulation method according to claim 17, wherein the previous weighting factors of the optimized outcome results from previous administered treatments are from another user.

20. The brain stimulation method according to claim 17, wherein the at least one biological metric measurement value is a measurement of an intrinsic frequency of a predefined electroencephalogram band.

21. The brain stimulation method according to claim 20, wherein the predefined electroencephalogram band is an alpha band, theta band, gamma band, beta band, or mu band.

22. The brain stimulation method according to claim 17, wherein the at least one biological metric measurement value is a measurement of an electroencephalogram alpha power of a predefined electroencephalogram band.

23. The brain stimulation method according to claim 17, wherein the at least one biological metric measurement value is a measurement of a Q-factor of a pre-defined intrinsic frequency of a predefined electroencephalogram band.

24. The brain stimulation method according to claim 17, wherein the at least one biological metric measurement value is a measurement of coherence of an electroencephalogram across a plurality of locations on the brain of the user.

25. The brain stimulation method according to claim 17, wherein the at least one biological metric measurement value is a measurement of phase of an electroencephalogram across a plurality of locations on the brain of the user.

26. The brain stimulation method according to claim 17, wherein the at least one biological metric measurement value is a ratio of a power of a first predefined electroencephalogram band and a power of a second predefined electroencephalogram band.

27. The brain stimulation method according to claim 17, wherein the at least one biological metric measurement value is a measurement of heart rate variability.

28. The brain stimulation method according to claim 17, wherein the at least one biological metric measurement value is a measurement of breathing rate variability.

29. The brain stimulation method according to claim 17, wherein the optimized outcome results are changes in value of measurements of at least one of:
   a psychological rating scale,
   a biological metric,
   a cognitive battery test score, or
   a Quality of Life rating scale score.

30. The brain stimulation method according to claim 29, wherein the outcome results are changes in value of measurements recorded before and after one or more treatment sessions.

31. The brain stimulation method according to claim 17, wherein the plurality of weighting factors are determined based on iterative optimization.

32. The brain stimulation method according to claim 17, wherein the plurality of weighting factors are determined based on stochastic optimization.

33. A non-transitory computer-readable storage medium storing computer-executable instructions, the computer-readable instructions, when executed by at least one hardware processor, cause the at least one hardware processor to perform steps, comprising:
   receiving at least one biological metric measurement value of a user;
   determining a treatment pulse frequency equal to a weighted sum of the at least one biological metric measurement value of the user,
   wherein the weighted sum includes a plurality of weighting factors individually corresponding to one of the at least one biological metric measurement values, and
   wherein the plurality of weighting factors are determined based on optimized outcome results from previous administered treatments using treatment pulse frequencies determined by previous weighting factors; and
   controlling a motor to operate at the determined treatment pulse frequency.

* * * * *